(12) United States Patent
Li et al.

(10) Patent No.: US 11,684,803 B2
(45) Date of Patent: Jun. 27, 2023

(54) POSITIONING METHOD AND APPARATUS, AND RADIATION THERAPY SYSTEM

(71) Applicant: Shenzhen OUR New Medical Technologies Development Co., Ltd., Shenzhen (CN)

(72) Inventors: Jinsheng Li, Shenzhen (CN); Pengfei Zhang, Shenzhen (CN)

(73) Assignee: Shenzhen OUR New Medical Technologies Development Co., Ltd., Shenzhen (CN)

( * ) Notice: Subject to any disclaimer, the term of this patent is extended or adjusted under 35 U.S.C. 154(b) by 13 days.

(21) Appl. No.: 16/931,928

(22) Filed: Jul. 17, 2020

(65) Prior Publication Data
US 2020/0346036 A1   Nov. 5, 2020

Related U.S. Application Data

(63) Continuation of application No. PCT/CN2018/089995, filed on Jun. 15, 2018.

(30) Foreign Application Priority Data

Jan. 19, 2018   (WO) ................ PCT/CN2018/073428

(51) Int. Cl.
*A61N 5/10*   (2006.01)
(52) U.S. Cl.
CPC ......... *A61N 5/1039* (2013.01); *A61N 5/1065* (2013.01); *A61N 5/1081* (2013.01)

(58) Field of Classification Search
CPC .. A61N 5/1039; A61N 5/1065; A61N 5/1081; A61N 2005/1097; A61N 5/1084; A61N 5/1049; A61B 6/04
See application file for complete search history.

(56) References Cited

U.S. PATENT DOCUMENTS

| 5,117,829 A * | 6/1992 | Miller .................... A61B 6/08 |
|---|---|---|
| | | 250/396 R |
| 2005/0180544 A1 | 8/2005 | Sauer et al. |

(Continued)

FOREIGN PATENT DOCUMENTS

| CN | 101537230 | 9/2009 |
|---|---|---|
| CN | 101843500 | 9/2010 |

(Continued)

*Primary Examiner* — Marcus H Taningco
(74) *Attorney, Agent, or Firm* — Emerson, Thomson & Bennett, LLC; Roger D. Emerson; Warren A. Rosborough

(57) ABSTRACT

Embodiments of the present disclosure provide a positioning method and apparatus, and a radiation therapy system. The positioning method comprises: acquiring a current gamma angle before radiation beams of a radiation source illuminate a treatment body part; acquiring a reconstructed image corresponding to the current gamma angle, the reconstructed image being an image reconstructed according to an image of the treatment body part acquired in advance; acquiring an IGRT image of the treatment body part corresponding to the current gamma angle, the IGRT image being an image generated by an image guide system; and comparing the reconstructed image with the IGRT image to obtain a deviation of the position of the treatment body part, and sending out the deviation, so that the position of the treatment body part is adjusted according to the deviation when the deviation is greater than a preset threshold.

20 Claims, 7 Drawing Sheets

(56) References Cited

U.S. PATENT DOCUMENTS

| | | | | |
|---|---|---|---|---|
| 2006/0050848 | A1* | 3/2006 | Vilsmeier | A61B 6/584 378/68 |
| 2014/0334709 | A1* | 11/2014 | Siewerdsen | G06T 7/32 382/132 |
| 2015/0272530 | A1* | 10/2015 | Umekawa | A61B 6/5264 378/7 |
| 2019/0201109 | A1* | 7/2019 | Berlinger | A61B 5/1127 |

FOREIGN PATENT DOCUMENTS

| | | |
|---|---|---|
| CN | 102232835 | 11/2011 |
| CN | 102697560 A | 10/2012 |
| CN | 202620501 | 12/2012 |
| CN | 104759033 A | 7/2015 |
| CN | 104888356 | 9/2015 |
| CN | 106714905 | 5/2017 |
| EP | 2248552 | 11/2010 |
| EP | 2662115 A1 | 11/2013 |
| WO | WO-2019141138 A1 * | 7/2019 ........... A61N 5/1067 |

\* cited by examiner

POSITIONING METHOD AND APPARATUS, AND RADIATION THERAPY SYSTEM

CROSS-REFERENCE TO RELATED APPLICATION

This application is a continuation of International Application No. PCT/CN2018/089995 filed on Jun. 5, 2018 and entitled "POSITIONING METHOD AND APPARATUS, AND RADIATION THERAPY SYSTEM". The International Application claims priority to PCT Application No. PCT/CN2018/073428, filed on Jan. 19, 2018 and entitled "POSITIONING METHOD AND APPARATUS, AND RADIATION THERAPY SYSTEM". The entire disclosures of the prior applications are hereby incorporated by reference in their entirety.

TECHNICAL FIELD

The present disclosure relates to the field of radiation therapy technology, in particular to a positioning method and apparatus, and a radiation therapy system.

BACKGROUND

Before radiation therapy, an image guide radiation therapy (IGRT) system is generally used to position a patient. When positioning, an IGRT image acquired by the IGRT system may be compared with a pre-acquired Computed Tomography (CT) image of a treatment body part (for example, the CT image of the treatment body part may be acquired by a CT-simulation localization machine), to determine a position relationship between an imaging point of the IGRT system and a predetermined point (also referred to as a preset filming point) in the CT image. Then, the imaging point may be aligned with the filming point by adjusting the position of a treatment couch, to position a patient. During radiation therapy, the relative position relationship between a beam focus and a target region may be determined according to the relative position relationship between the imaging point and the beam focus of a radiation source, and the relative position relationship between the preset filming point in the CT image and the target region, and finally the position of the treatment couch may be adjusted according to the relative position relationship between the beam focus and the target region, so that the target region is aligned with the beam focus to facilitate the radiation therapy.

During the radiation therapy, in order to avoid the influence of a treatment beam on sensitive tissues or organs (for example, eyes) other than the treatment body part, the patient's position is generally adjusted by adjusting a gamma angle of the radiation therapy system, so that the treatment beam can avoid sensitive parts. The gamma angle may refer to an angle between a supporting plane and a vertical plane of a fixing structure for supporting the patient and located at the bottom of the patient.

However, because the patient usually lies when the CT image is shoot, the gamma angle is constant. If the gamma angle needs to be adjusted during the radiation therapy, the accuracy of positioning by the IGRT system according to the CT image will be greatly reduced, which seriously affects the effect of radiation therapy.

SUMMARY

The present disclosure provides a positioning method and apparatus, and a radiation therapy system, which can solve the problem of low accuracy of positioning methods in related technologies. The technical solutions are as follows:

In a first aspect, a positioning method is provided, applied to an image guide system, the method including:

acquiring a current gamma angle before radiation beams of a radiation source illuminate a treatment body part;

acquiring a reconstructed image corresponding to the current gamma angle, the reconstructed image being an image reconstructed according to an image of the treatment body part acquired in advance;

acquiring an IGRT image of the treatment body part corresponding to the current gamma angle, the IGRT image being an image generated by an image guide system; and comparing the reconstructed image with the IGRT image to obtain a deviation of a position of the treatment body part, and send out the deviation, so that the position of the treatment body part is adjusted according to the deviation when the deviation is greater than a preset threshold.

In a second aspect, another positioning method is provided, applied to a computer in a radiation therapy system, the method including:

receiving a deviation of a position of a treatment body part sent by an image guide system, the deviation being obtained by comparing a reconstructed image corresponding to a current gamma angle with an IGRT image of the treatment body part corresponding to the current gamma angle after the reconstructed image and the IGRT image are acquired by the image guide system, and the reconstructed image being an image reconstructed according to an image of the treatment body part acquired in advance; and adjusting the position of the treatment body part according to the deviation when the deviation is greater than a preset threshold.

In a third aspect, an image guide system is provided, the image guide system including: a processor and a memory, where the memory is configured to store instructions executed by the processor, and the processor is configured to perform operations of:

acquiring a current gamma angle before radiation beams of a radiation source illuminate a treatment body part;

acquiring a reconstructed image corresponding to the current gamma angle, the reconstructed image being an image reconstructed according to an image of the treatment body part acquired in advance;

acquiring an IGRT image of the treatment body part corresponding to the current gamma angle, the IGRT image being an image generated by the image guide system; and comparing the reconstructed image with the IGRT image to obtain a deviation of a position of the treatment body part, and send out the deviation, so that the position of the treatment body part is adjusted according to the deviation when the deviation is greater than a preset threshold.

In a fourth aspect, a computer is provided, applied to a radiation therapy system. The computer includes: a processor and a memory, where the memory is configured to store instructions executed by the processor, and the processor is configured to perform operations of:

receiving a deviation of a position of a treatment body part sent by an image guide system, the deviation being obtained by comparing a reconstructed image corresponding to the current gamma angle with an IGRT image of the treatment body part corresponding to the current gamma angle after the reconstructed image and the IGRT image are acquired by the image guide system, and the reconstructed image being an image reconstructed according to an image of the treatment body part acquired in advance; and adjusting the position of the treatment body part according to the deviation when the deviation is greater than a preset threshold. The computer may be a host computer in the radiation therapy system.

In a fifth aspect, a radiation therapy system is provided, the system including: the computer according to the fourth aspect and the image guide system according to the third aspect, the computer establishing a communication connection with the image guide system.

In a sixth aspect, a computer-readable storage medium is provided, the computer-readable storage medium storing instructions. When the computer-readable storage medium runs on a computer, the computer is enabled to perform the positioning method according to the first aspect or the positioning method according to the second aspect.

Based on the above, the embodiments of the present disclosure provide a positioning method and apparatus, and a radiation therapy system, in which an image guide system may acquire, after acquiring a current gamma angle, a reconstructed image corresponding to the current gamma angle, the reconstructed image corresponding to the current gamma angle being an image reconstructed according to an image of a treatment body part; and then the image guide system may determine a deviation of the position of the treatment body part by comparing an IGRT image corresponding to the current gamma angle with the reconstructed image, and send out the deviation, so that an adjustment device can adjust the position of the treatment body part according to the deviation when the deviation is greater than a preset threshold, to position the patient. Since the image referenced by the image guide system when obtaining the deviation is a reconstructed image corresponding to the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced as much as possible.

It should be understood that the above general description and the following detailed description are merely exemplary and explanatory, and should not limit the present disclosure.

BRIEF DESCRIPTION OF THE DRAWINGS

In order to more clearly illustrate the technical solutions in the embodiments of the present disclosure, the drawings used in the description of the embodiments will be briefly described below. Obviously, the drawings in the following description are only some embodiments of the present disclosure, and those of ordinary skill in the art may obtain other drawings according to the drawings without any creative efforts.

Specific embodiments of the present disclosure have been shown through the above drawings, and more details are described below. These drawings and text descriptions are not intended to limit the scope of the inventive concept in any way, but to explain the concept of the present disclosure to those skilled in the art by referring to the specific embodiments.

DETAILED DESCRIPTION

To make the objectives, technical solutions and advantages of the present disclosure clearer, the following further describes the embodiments of the present invention in detail with reference to the accompanying drawings.

Figure 1:
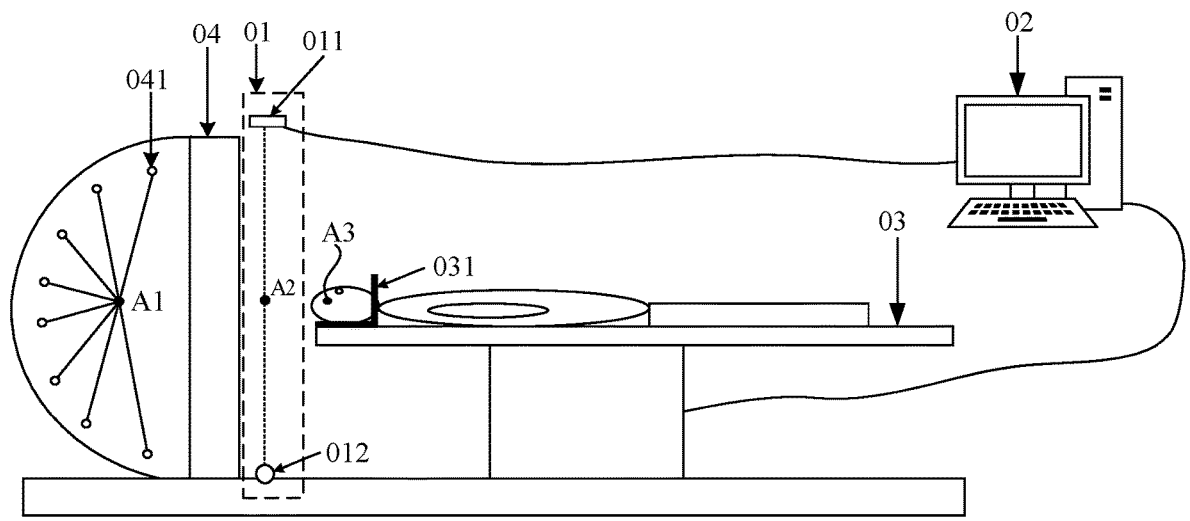
FIG. 1 is a schematic structural diagram of a radiation therapy system according to an embodiment of the present disclosure.

FIG. 1 is a schematic structural diagram of a radiation therapy system according to an embodiment of the present disclosure. As shown in FIG. 1, the radiation therapy system may include an image guide system 01, a computer 02, a treatment couch 03, and a treatment gantry 04. The computer 02 establishes a communication connection with the image guide system 01 and the treatment couch 03, respectively. The computer 02 may also be a control device in a treatment control system, the treatment control system may be a radiotherapy record and verification system (RVS), and the image guide system 01 may be an IGRT system.

A plurality of radiation sources 041 are arranged in the treatment gantry 04, and treatment beams emitted by the plurality of radiation sources 041 may intersect at a point, which is a beam focus (also referred to as a treatment point) A1. The image guide system 01 may include multiple sets of image acquisition units, each set of image acquisition unit may include a detector 011 and a bulb 012 arranged oppositely, the bulb 012 may emit rays (for example, X-rays), the detector 011 may be a flat panel detector, and the detector 011 may receive the rays emitted by the bulb 012. The image guide system 01 may generate an IGRT image according to the rays received by each detector 011. The rays emitted by the bulbs 012 in the multiple sets of image acquisition unit of the IGRT system may intersect at a point, which is an imaging point A2 of the IGRT system. In this application, the image guide system 01 is an IGRT system, and the IGRT system includes two sets of image acquisition units as an example for description. The rays emitted by the bulbs 012 of the two sets of image acquisition units may intersect at the imaging point A2.

The process of positioning using the IGRT system is as follows:

Step S1, a patient is fixed on the treatment couch using a positioning device, and CT scanning is performed on the patient to acquire a CT image of the patient.

Step S2, a treatment plan for a treatment body part is made by a therapist according to the size, shape and surrounding tissues of a treatment body part tumor displayed in the CT image, the treatment plan is input to the computer 02, and the CT image and other information required by the IGRT system are transmitted to the IGRT system in a file format such as DICOM RT (a transmission standard of radiation therapy data).

Step S3, the computer retrieves and confirms the patient's treatment plan, and the IGRT system also loads the patient's IGRT plan information.

Step S4, the patient enters a radiotherapy room, and the therapist fixes the patient on the treatment couch through a fixing device, and begins to position the patient. Exemplarily, the fixing device may be a head frame, a dental tray or a mask.

The process of positioning using the IGRT system may specifically include:

S41, the computer 02 adjusts the position of the treatment couch 03 to move the treatment body part of the patient to an imaging area of the IGRT system 01, so as to acquire an IGRT image.

S42, the IGRT system 01 compares the IGRT image with the CT image to determine the relative position relationship between a preset filming point in the CT image and the imaging point A2 of the IGRT system 01, and sends the relative position relationship to the computer 02.

The preset filming point in the CT image may be a fixed point predetermined in the CT image.

S43, the computer 02 adjusts the position of the treatment couch 03, so that the preset filming point of the CT image coincides with the imaging point A2 of the IGRT system 01.

S44, the computer 02 determines an offset between a target region A3 and the beam focus A1 according to the relative position relationship between the beam focus A1 and the imaging point A2 of the IGRT system 01, and the relative position relationship between the preset filming point in the CT and the target region A3, and adjusts the position of the treatment couch 03 according to the offset, so that the target region A3 is aligned with the beam focus A1 to position the patient.

Figure 2:
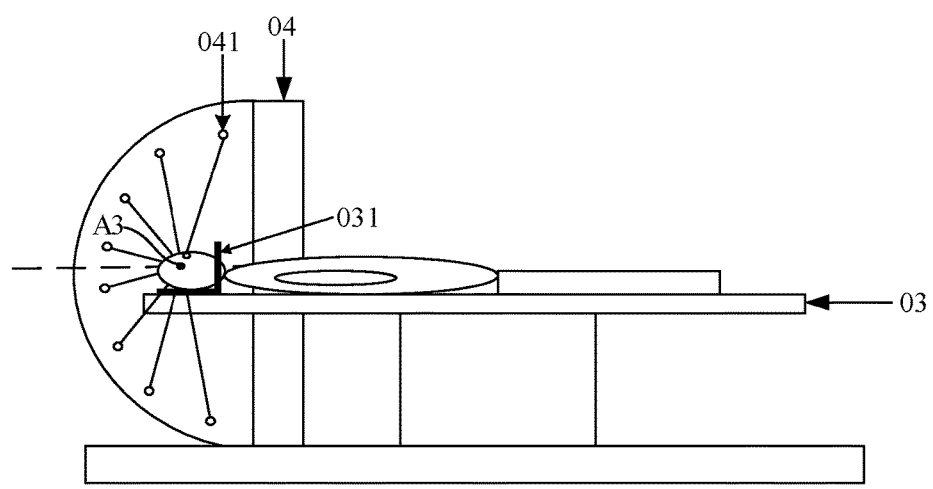
FIG. 2 is a schematic diagram of a position relationship between a target region and treatment beams in a radiation therapy process according to an embodiment of the present disclosure.
Figure 3:
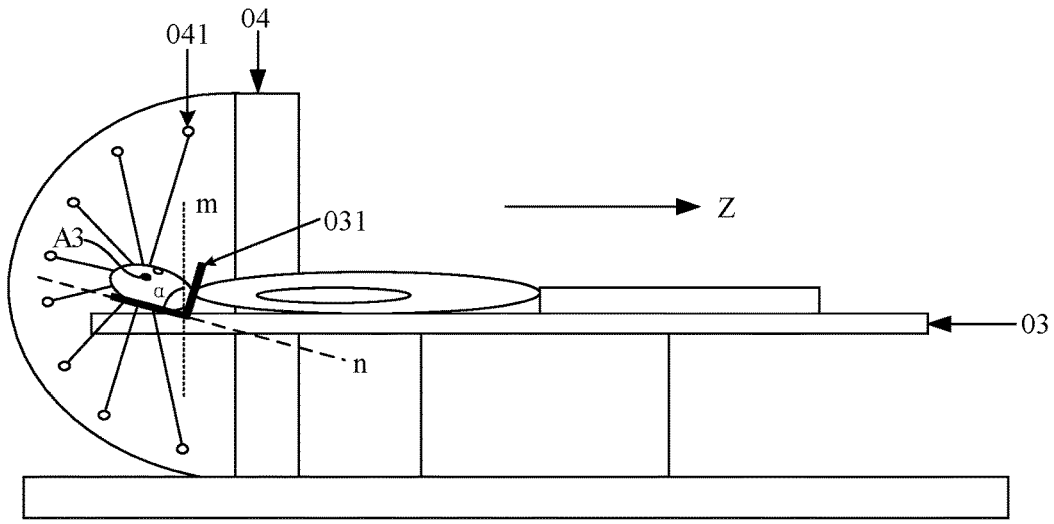
FIG. 3 is a schematic diagram of a position relationship between a target region and treatment beams in another radiation therapy process according to an embodiment of the present disclosure.

However, when the CT positioning scanning is performed on the patient in the above step S1, the patient generally lies on the treatment couch 03. In the actual treatment process, if the patient lies on the treatment couch 03, as shown in FIG. 2, the treatment beams may pass through the patient's sensitive tissues or organs, such as the eyes, to irradiate the target region A3. Therefore, as shown in FIG. 3, the therapist may adjust the patient's position through a fixing structure such as a head fixing device 031, so that the treatment beams avoid sensitive tissues or organs. In addition, the fixing structure may rotate about a fixed rotation axis within a vertical plane (i.e., a plane perpendicular to the horizontal plane), and the fixed rotation axis is parallel to the horizontal plane and perpendicular to a length direction Z of the treatment couch. The angle $\alpha$ between a supporting plane n (or a plane parallel to the supporting plane n and passing through the rotation axis) of a supporting portion for supporting the patient in the fixing structure, and the vertical plane m may be referred to as a gamma angle of the radiation therapy system.

Exemplarily, in the above step S1, the CT image is scanned while the patient lies (that is, the gamma angle $\alpha$ is 90°). In the actual treatment process, as shown in FIG. 3, the therapist chooses a gamma angle of 70° for treatment. When the IGRT system is used for positioning, the head fixing device 031 needs to be adjusted so that the patient is at the gamma angle of 70°, and then an IGRT image is acquired. At this time, if the IGRT system 01 directly compares the CT image with the IGRT image, because the deflection angle of the patient's position is different, the offset cannot be obtained, and accurate treatment cannot be achieved accordingly.

Before the CT image of the patient is shot, the therapist cannot determine the gamma angle used in the actual treatment process, so if multiple gamma angles are used to shoot CT images in advance, for example, CT images at the gamma angles of 70°, 90° and 110° are shot respectively, then in the actual treatment process, the IGRT selects the CT image of the corresponding gamma angle to position, and the error of the calculated offset can be guaranteed. But this will significantly increase the radiation dose received by the patient, which is not conducive to the patient's health and will additionally increase the patient's treatment costs.

Figure 4:
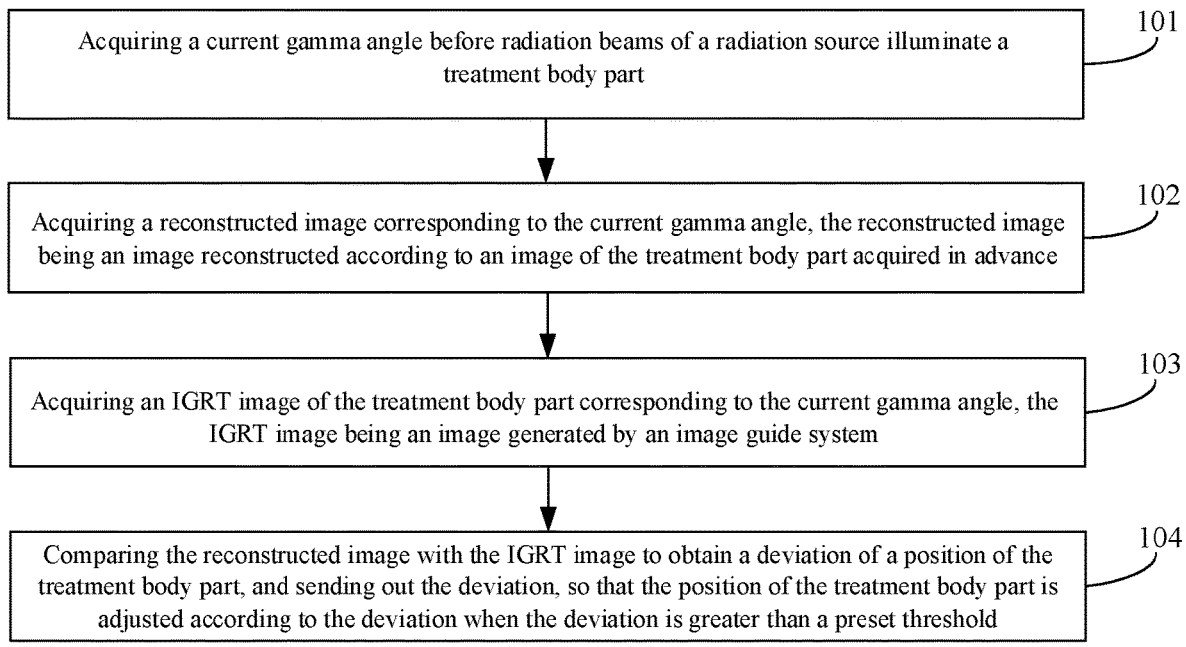
FIG. 4 is a flowchart of a positioning method according to an embodiment of the present disclosure.

FIG. 4 is a flowchart of a positioning method provided by an embodiment of the present disclosure. The method may be applied to the image guide system 01 shown in FIG. 1, for example, the IGRT system. Referring to FIG. 4, the method may include steps S101 to S104 that follows.

Step 101, a current gamma angle is acquired before radiation beams of a radiation source illuminate a treatment body part.

In an optional implementation manner of the embodiment of the present disclosure, the image guide system may acquire a treatment plan in advance, the treatment plan may include at least one gamma angle, and the image guide system may determine the current gamma angle from the at least one gamma angle. For example, after the radiation therapy system completes positioning and treatment at a certain gamma angle, the image guide system may determine next gamma angle in the treatment plan as the current gamma angle.

In another optional implementation manner of the embodiment of the present disclosure, the image guide system may also directly receive the current gamma angle sent by the computer. For example, when the therapist fixes the patient to a certain gamma angle through a fixing structure, the therapist can input the current gamma angle to the computer; or the computer can also determine the current gamma angle according to the treatment plan acquired in advance. After the computer determines the current gamma angle, it can send the current gamma angle to the image guide system.

Step 102, a reconstructed image corresponding to the current gamma angle is acquired.

The reconstructed image may be an image reconstructed according to an image (for example, a CT image or a nuclear magnetic resonance image, etc.) of the treatment body part acquired in advance. Moreover, the reconstructed image may be an image reconstructed by the image guide system according to an image, or an image reconstructed by an image generating device (for example, a CT device) according to the image, or a reconstructed image generated by other image processing system according to an image. The embodiment of the present disclosure does not limit the device for generating the reconstructed image.

Optionally, the reconstructed image may be a digitally reconstructed radiograph (DRR) image, and the DRR image may be an image reconstructed by the IGRT system according to a CT image of the treatment body part after acquiring the CT image.

Exemplarily, in the embodiment of the present disclosure, the IGRT system may reconstruct, after acquiring a CT image of the treatment body part, DRR images of multiple gamma angles according to the CT image. After the current gamma angle is acquired, the IGRT system may retrieve a DRR image corresponding to the current gamma angle from the multiple DRR images. For example, the IGRT system may reconstruct DRR images of 60°, 70°, 80°, 90°, 100°, and 110° according to the CT image. If the current gamma angle is 70°, the IGRT system may retrieve a DRR image corresponding to the gamma angle of 70°.

Step 103, an IGRT image of the treatment body part corresponding to the current gamma angle is acquired.

Further, the computer may adjust the position of the treatment couch according to a preset fixed coordinate value, and transfer the treatment body part of the patient to the imaging area of the IGRT system. Since the patient is already fixed at the current gamma angle, the image guide system may directly acquire the IGRT image of the treatment body part corresponding to the current gamma angle through multiple sets of image acquisition units.

For example, in this disclosure, the computer may send an imaging instruction to the IGRT system, the IGRT system may control the bulb 012 to emit rays (for example, X-rays), the detector 011 may receive the rays emitted by the bulb 012, and the IGRT system 01 may generate an IGRT image according to the rays received by each detector 011.

Step 104, the reconstructed image is compared with the IGRT image to obtain a deviation of the position of the treatment body part and send it out.

Further, the image guide system may obtain the deviation of the position of the treatment body part by comparing the reconstructed image with the IGRT image, and send the deviation to an adjustment device, so that the adjustment device can adjust the position of the treatment body part according to the deviation when the deviation is greater than a preset threshold. For example, the image guide system may send the deviation to the computer. When the deviation is greater than the preset threshold, the computer may adjust the position of the treatment couch according to the deviation, and then adjust the position of the treatment body part to position the patient.

For example, the image guide system may determine a first offset between a filming point of the reconstructed image and an imaging point of the IGRT system by comparing the reconstructed image (e.g., the DRR image) with the IGRT image, and send the first offset to the computer as the deviation.

The filming point of the reconstructed image is determined according to a filming point of an image (for example, a CT image), and the filming point of the reconstructed image is also a fixed point in the reconstructed image, for example, a center point of the reconstructed image. Correspondingly, after the adjustment device (for example, the computer) adjusts the position of the treatment body part according to the deviation, the filming point may be aligned with the imaging point to position the patient. Afterwards, during radiation therapy, the adjustment device may determine the relative position relationship between the target region and the beam focus according to the relative position relationship between the filming point and the target region, and the relative position relationship between the imaging point and the beam focus, so that the target region can be aligned with the beam focus by adjusting the treatment couch.

Based on the above, the embodiment of the present disclosure provides a positioning method, in which an image guide system may acquire, after acquiring a current gamma angle, a reconstructed image corresponding to the current gamma angle, the reconstructed image corresponding to the current gamma angle being an image reconstructed by the image guide system in advance according to an image of a treatment body part; and then the image guide system may determine a deviation of the position of the treatment body part by comparing an IGRT image corresponding to the current gamma angle with the reconstructed image, and send out the deviation, so that an adjustment device can adjust the position of the treatment body part according to the deviation when the deviation is greater than a preset threshold, to position the patient. Since the image referenced by the image guide system when calculating the deviation is a reconstructed image reconstructed according to an image and corresponding to the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced as much as possible.

Figure 5:
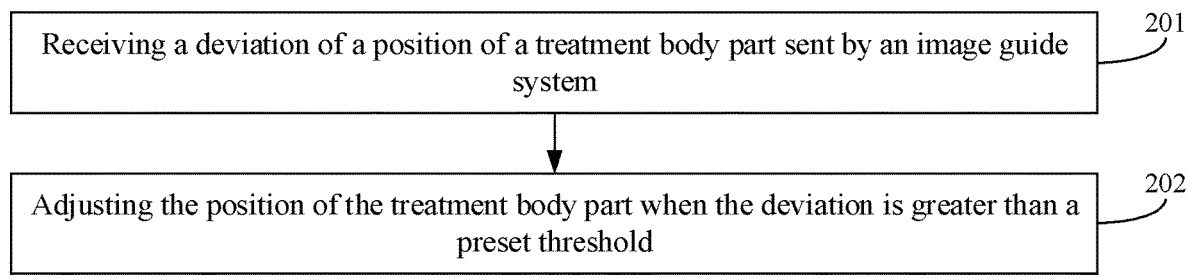
FIG. 5 is a flowchart of another positioning method according to an embodiment of the present disclosure.

FIG. 5 is a flowchart of another positioning method provided by an embodiment of the present disclosure. The method may be applied to the computer 02 shown in FIG. 1. Referring to FIG. 5, the method may include steps 201 and 202 that follows.

Step 201, a deviation of a position of a treatment body part sent by an image guide system is received.

The deviation is obtained by comparing a reconstructed image corresponding to the current gamma angle with an IGRT image of the treatment body part corresponding to the current gamma angle after the reconstructed image and the IGRT image are acquired by the image guide system, the reconstructed image being an image reconstructed according to an image of the treatment body part acquired in advance.

In the embodiment of the present disclosure, after a therapist fixes a patient at a certain gamma angle through a fixing structure, the therapist may input the current gamma angle to the computer, and the computer may then send the current gamma angle to the image guide system, so that the image guide system can acquire the reconstructed image and the IGRT image corresponding to the current gamma angle, and obtain the deviation of the position of the treatment body part.

Alternatively, the computer may also determine, after receiving a treatment plan sent by a treatment plan system (TPS), the current gamma angle according to at least one gamma angle included in the treatment plan, and send the current gamma angle to the image guide system. For example, the computer may determine, after the radiation therapy system completes positioning and treatment of a certain gamma angle, next gamma angle in the treatment plan as the current gamma angle.

Step 202, the position of the treatment body part is adjusted when the deviation is greater than a preset threshold.

Further, the computer may detect whether the deviation is greater than a preset threshold, and if the deviation is greater than the preset threshold, the computer may adjust the position of a treatment couch according to the deviation, to adjust the position of the treatment body part, and thus to position the patient; and if the deviation is not greater than the preset threshold, the computer may determine that the position of the treatment body part has met the requirement of treatment precision, so no further adjustment is required.

Exemplarily, if the deviation is a first offset between a filming point in the reconstructed image and an imaging point of the IGRT system, the computer may adjust the position of the treatment couch according to the deviation to align the filming point with the imaging point. Further, the position of the imaging point of the IGRT system and the position of the beam focus of the radiation source are fixed, so during radiation therapy, the computer may also determine a second offset between a target region and the beam focus according to the relative position relationship between the imaging point and the beam focus, and the relative position relationship between the filming point in the image and the target region. The computer then adjusts the position of the treatment couch according to the second offset, to align the target region with the beam focus, so as to begin the radiation therapy.

Based on the above, the embodiment of the present disclosure provides a positioning method, in which a computer may receive a deviation sent by an image guide system, the deviation being obtained by comparing, after the image guide system acquires a reconstructed image corresponding to the current gamma angle, an IGRT image corresponding to the current gamma angle with the reconstructed image; and the computer may adjust the position of the treatment body part according to the deviation when the deviation is greater than a preset threshold. Since the image referenced by the image guide system when calculating the deviation is a reconstructed image reconstructed according to an image and corresponding to the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced as much as possible.

Figure 6:
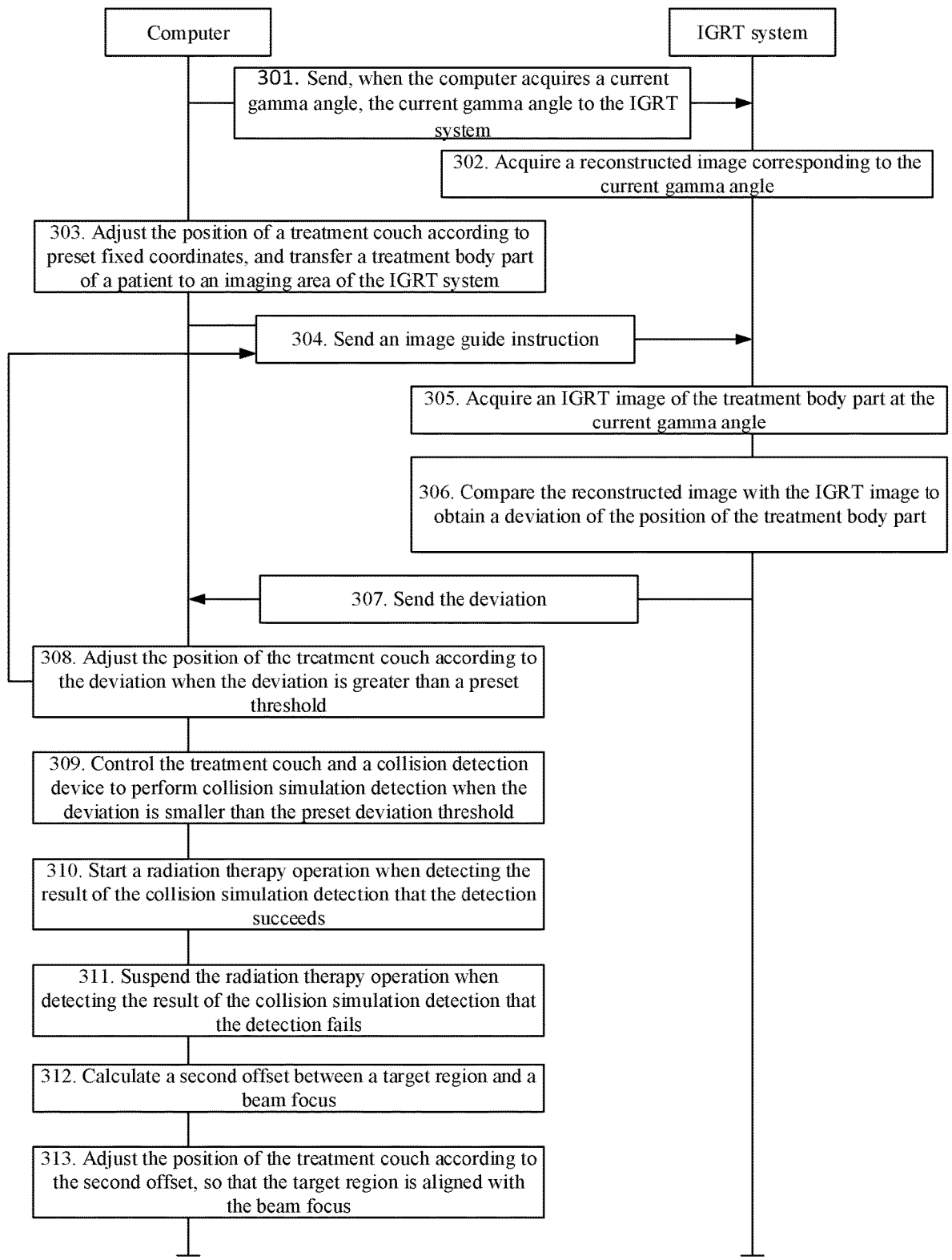
FIG. 6 is a flowchart of still another positioning method according to an embodiment of the present disclosure.

FIG. 6 is a flowchart of yet another positioning method provided by an embodiment of the present disclosure. The method may be applied to the radiation therapy system shown in FIG. 1, the image guide system 01 in the radiation therapy system is an IGRT system as an example, and referring to FIG. 6, the method may include steps 301 to 311 that follows.

Step 301, a computer sends, when acquiring a current gamma angle, the current gamma angle to the IGRT system.

In the embodiment of the present disclosure, exemplarily, after determining a treatment plan, a TPS may transmit an Extensible Markup Language (XML) file of the treatment plan to the computer, and transmit a DICOM RT (a transmission standard of radiation therapy data) file to the IGRT system. The XML file sent by the TPS to the computer may include at least one gamma angle for treatment, and coordinates of a filming point and a target region in an image (e.g., a CT image).

During the positioning process, after fixing a patient to a certain gamma angle through a fixing structure (for example, the head fixing device 031 shown in FIG. 1), the therapist may input the current gamma angle to the computer, and computer may send, after acquiring the current gamma angle, the current gamma angle to the IGRT system. The computer may be, for example, a host computer in the radiation therapy system.

For example, if the current gamma angle is 70°, the therapist may adjust the head fixing device 031 shown in FIG. 1, so that the current gamma angle of the patient is 70°. After completing the fixation of the head fixing device 031, the therapist may input the current gamma angle of 70° to the computer, and the computer may then send the current gamma angle of 70° to the IGRT system.

It should be noted that, in the embodiment of the present disclosure, the computer may also acquire the current gamma angle in other ways before radiation beams of a radiation source illuminate the treatment body part, for example, directly acquire the current gamma angle from the treatment plan. Or, the computer may directly detect the current gamma angle after the therapist adjusts the gamma angle through the fixing structure. The embodiment of the present disclosure does not limit the manner in which the computer acquires the current gamma angle.

Step 302, the IGRT system acquires a reconstructed image corresponding to the current gamma angle.

In the embodiment of the present disclosure, the DICOM RT file sent by the TPS system to the IGRT system may include at least one gamma angle for treatment, and an image (for example, a CT image) obtained by scanning the treatment body part of the patient in advance. After receiving the DICOM RT file sent by the TPS system, the IGRT system may reconstruct, according to the image, a reconstructed image corresponding to each of the at least one gamma angle.

Optionally, the image sent by the TPS system may be a plurality of consecutive CT images obtained by scanning the treatment body part with a CT device, that is, the image may be an image sequence. Each CT image in the image sequence is perpendicular to a horizontal axis of a treatment couch, and the extension direction of the horizontal axis may be parallel to a movement direction (i.e., an advancing direction) of the treatment couch when moving closer to a treatment room. Since each CT image is a two-dimensional image, the plurality of consecutive CT images may be reconstructed into three-dimensional volume data of the treatment body part by the processing of the computer. Optionally, the layer thickness when the CT device scans the treatment body part may not be more than 2 mm, and there is no interlayer spacing.

In the process of reconstructing the image, the IGRT system may first determine a rotation axis according to a preset filming point in the image. The rotation axis may be a designated coordinate axis of a coordinate system where the filming point is located, or a linear axis parallel to the designated coordinate axis. For example, in the coordinate system where the filming point is located, the linear axis that passes through the filming point and is parallel to the designated coordinate axis (for example, X axis) may be determined as the rotation axis. Further, for each gamma angle, the IGRT system may rotate the image about the rotation axis by a deflection angle, thereby reconstructing the reconstructed image corresponding to the gamma angle. The deflection angle is a deflection angle between this gamma angle and the gamma angle when the image is acquired. Specifically, the IGRT system may rotate the three-dimensional volume data corresponding to the plurality of CT images about the rotation axis by the deflection angle, and project the rotated three-dimensional volume data to a virtual imaging plane of the IGRT system according to the installation parameters of the IGRT system to obtain the reconstructed image corresponding to the gamma angle.

The filming point in the image is a preset point in the image, and the position of the filming point may be described by coordinates of three coordinate axes in a three-dimensional coordinate system (for example, a DICOM coordinate system) where the filming point is located. The virtual imaging plane is an imaging plane of the IGRT system virtually constructed in the coordinate system where the filming point is located, and the position of the virtual imaging plane in the three-dimensional coordinate system where the filming point is located is the same as the position of an imaging plane of a detector in the IGRT system in a coordinate system (also referred to as a device coordinate system) where the treatment couch is located.

Optionally, as mentioned above, the IGRT system may include multiple sets of image acquisition units, and each set of image acquisition unit may include a detector and a bulb arranged oppositely. Since the installation parameters of each set of image acquisition unit affect the virtual imaging plane of the IGRT system when generating a DRR image, before the rotated three-dimensional volume data is projected to the virtual imaging plane of the IGRT system, the IGRT system may also determine, according to the installation parameters of the image acquisition unit, the position of the virtual imaging plane of the IGRT system in the coordinate system where the filming point is located. The installation parameters may include: the angle between rays of two sets of image acquisition units, the distance between the detector and the bulb in each set of image acquisition unit, the distance between the intersection point of the rays and the detector, etc. The ray of each set of image acquisition unit may be the connection line between the detector and the bulb in the set of image acquisition unit, and the imaging plane of the detector is perpendicular to the ray emitted by the bulb.

It should be noted that when the three-dimensional volume data is rotated to reconstruct a reconstructed image corresponding to a certain gamma angle, the rotation direction of the three-dimensional volume data may be determined according to the deflection direction of the gamma angle relative to the gamma angle during the image acquisition, to ensure that the rotation direction of the three-dimensional volume data in the image coordinate system (for example, the DICOM coordinate system) is consistent with the deflection direction of the gamma angle in the coordinate system where the treatment couch is located, and their deflection angles are also consistent.

Further, after receiving the current gamma angle sent by the computer, the IGRT system may retrieve a reconstructed image corresponding to the current gamma angle from the previous reconstructed image corresponding to the at least one gamma angle.

For example, assuming that the gamma angles used for treatment in the treatment plan include 70°, 90°, and 110°, after receiving the DICOM RT file sent by TPS, the IGRT system may reconstruct a DRR image of the 70° gamma angle, a DRR image of the 90° gamma angle, and a DRR image of the 110° gamma angle according to the CT image. When it is detected that the current gamma angle sent by the computer is 70°, the IGRT system may extract the DRR image corresponding to the 70° gamma angle from the three DRR images reconstructed in advance.

Figure 7:
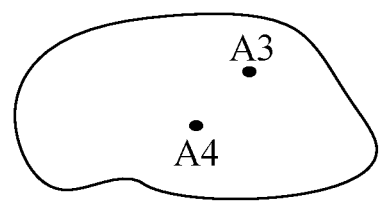
FIG. 7 is a schematic diagram of a relative position relationship between a preset point (also referred to as a filming point) in a CT image and a target region according to an embodiment of the present disclosure.

If the CT image is obtained by scanning when the patient lies (that is, the gamma angle is 90°), the relative position relationship between the filming point A4 preset in the CT image and the target region A3 may be as shown in FIG. 7.

Figure 8:
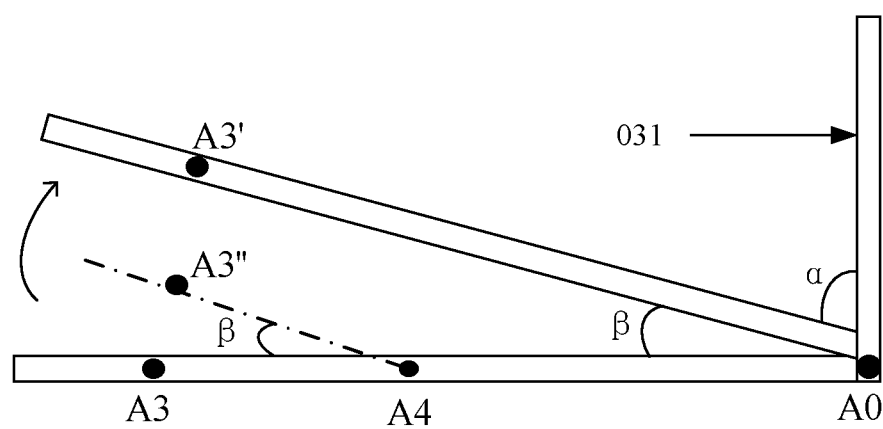
FIG. 8 is a schematic diagram of a relative position relationship between a target region in a DRR (Digitally Reconstructed Radiograph) image and an actual target region according to an embodiment of the present disclosure.

When the current gamma angle is 70°, referring to FIG. 8, the deflection angle between the current gamma angle and the gamma angle when the CT image is acquired is β, and β=20°. Then, when reconstructing the DRR image corresponding to the 70° gamma angle, the IGRT system may deflect the three-dimensional volume data corresponding to the CT image by 20° based on the preset filming point A4 in the CT image as a center point and the straight line passing through the filming point in the DICOM coordinate system and parallel to the X axis as an axis, and project the rotated three-dimensional volume data to the virtual imaging plane in the IGRT to obtain the DRR image corresponding to the 70° gamma angle. At this time, the coordinate of the target region A3 in the DRR image is updated to A3".

However, during actual treatment, the rotation point A of a bracket in the head fixing device 031 does not coincide with the preset filming point A4 in the CT image, so after the therapist rotates the bracket for supporting the patient in the head fixing device 031 by 20°, the target region A3 will move to A3'. It can be seen from FIG. 8 that the target region A3" in the DRR image does not coincide with the actual target region A3', and there is a certain deviation between the two, so the deviation between the two further needs to be reduced by adjusting the position of the treatment couch.

Step 303, the computer adjusts the position of a treatment couch according to preset fixed coordinates, and transfers a treatment body part of a patient to an imaging area of the IGRT system.

In the embodiment of the present disclosure, since the position of the imaging point of the IGRT system is a fixed position, fixed coordinates determined according to the coordinates of the imaging point may be pre-stored in the computer. When the treatment couch is at the fixed coordinates, it can be guaranteed that the treatment body part (the treatment body part includes the part corresponding to the filming point in the DRR image) of the patient is within the imaging area of the IGRT system.

Step 304, the computer sends an image guide instruction to the IGRT system.

After the computer completes adjusting the position of the treatment couch, the therapist may trigger the computer to send the image guide instruction to the IGRT system through a preset operation. For example, the computer may be provided with a touch display screen. After the computer completes adjusting the position of the treatment couch, an icon indicating the sending of the image guide instruction may be displayed on the touch display screen. When the therapist clicks the prompt icon, the computer may send the image guide instruction to the IGRT system, the image guide instruction being used to instruct the IGRT system to acquire an IGRT image.

Step 305, the IGRT system acquires an IGRT image of the treatment body part corresponding to the current gamma angle.

After receiving the image guide instruction sent by the computer, the IGRT system may acquire the IGRT image of the treatment body part corresponding to the current gamma angle through multiple sets of image acquisition units.

For example, since the patient is currently fixed at the gamma angle of 70°, the IGRT system may acquire the IGRT image of the treatment body part at the gamma angle of 70°.

Step 306, the IGRT system compares the reconstructed image with the IGRT image to obtain a deviation of the position of the treatment body part.

Further, the IGRT system may compare the acquired IGRT image with the reconstructed image corresponding to the current gamma angle to obtain the deviation of the position of the treatment body part. For example, the IGRT system may calculate a first offset between the filming point in the reconstructed image and the imaging point of the IGRT system by comparing the reconstructed image with the IGRT image, and use the first offset as the deviation of the position of the treatment body part.

In the embodiment of the present disclosure, the deviation may include translation data and angle data. The translation data may be three-dimensional translation data, that is, the translation data may include three sub-data, and each sub-data may be used to indicate an offset of the treatment couch in the preset three-dimensional coordinate system along each coordinate axis; the angle data may also be three-dimensional angle data, that is, the angle data may also include three sub-data, and each sub-data is used to indicate an amount of rotation of the treatment couch in the three-dimensional coordinate system within each plane.

For example, it is assumed that the translation data in the deviation calculated by the IGRT system is: X=2 millimeters (mm), Y=0, and Z=−1 mm; and the angle data is: XY=0, YZ=1°, and XZ=2°. Then, the translation data may be used to instruct the treatment couch to translate 2 mm in the positive direction of the X axis in the three-dimensional coordinate system, and to move 1 mm in the negative direction of the Z axis, without moving in the Y axis direction; and the angle data may be used to instruct the treatment couch to rotate 1 within the YZ plane defined by the Y axis and the Z axis, and to rotate 2° within the XZ plane defined by the X axis and the Z axis, without rotating within the XY plane.

It should be noted that, after the computer adjusts the position of the treatment couch and transfers the treatment body part to the imaging area of the IGRT system, if the therapist determines, by observing the reconstructed image and the first acquired IGRT image, that the deviation between the filming point of the reconstructed image and the imaging point of the IGRT image is large, the deviation may also be manually input directly in the IGRT system, so that the IGRT system can send the manually input deviation to the computer.

Optionally, in the embodiment of the present disclosure, when the IGRT system sends the deviation to the computer, the adjustment order of each angle in the angle data of the deviation may also be stated in the data sent, so that the computer can adjust each angle in turn according to the adjustment order.

It should be noted that, in the embodiment of the present disclosure, when the IGRT system includes multiple sets of image acquisition units, since each set of image acquisition unit can acquire an image (i.e., an X-ray image) of the treatment body part, the IGRT image acquired by the IGRT system may include multiple images of the treatment body part acquired by the multiple sets of image acquisition units.

Correspondingly, in the above step 302, for the multiple sets of image acquisition units, the IGRT system may determine a virtual imaging plane corresponding to the imaging plane of the detector in each set of image acquisition unit to obtain multiple virtual imaging planes. In addition, the IGRT system may project the rotated three-dimensional volume data to each virtual imaging plane to obtain a reconstructed image corresponding to each virtual imaging plane, that is, to obtain a reconstructed image corresponding to each set of image acquisition unit.

When the IGRT image is compared with the reconstructed image, the image of the treatment body part acquired by each set of image acquisition unit may be compared with the reconstructed image corresponding to the set of image acquisition unit to obtain a deviation. After the images of the treatment body part acquired by the various sets of image acquisition units are compared with the corresponding reconstructed images respectively, multiple deviations can be obtained. Finally, the IGRT system can comprehensively analyze and process the multiple deviations and determine a final deviation of the position of the treatment body part.

Step 307, the IGRT system sends the deviation to the computer.

For example, the IGRT system may send the deviation including the translation data and the angle data to the computer.

Step 308, the computer adjusts the position of the treatment body part according to the deviation when the deviation is greater than a preset threshold.

After receiving the deviation, the computer may first detect whether the deviation is greater than a preset threshold. If the deviation is greater than the preset threshold, the computer may adjust the position of the treatment couch according to the deviation to adjust the position of the treatment body part, and thus to position the patient. If the deviation is not greater than the preset threshold, the computer may determine that the position of the treatment body part has met the requirement of radiation therapy precision, so no further adjustment is required.

In the embodiment of the present disclosure, when the deviation is the first offset between the filming point in the reconstructed image and the imaging point of the IGRT system, the computer may adjust the position of the treatment couch according to the deviation, so that the filming point in the reconstructed image coincides with the imaging point of the IGRT system.

Further, the deviation may include translation data and angle data, and the treatment couch in the radiation therapy system may be a three-dimensional treatment couch (that is, the treatment couch can only be translated up and down, left and right, and front and back) or a six-dimensional treatment couch (that is, the treatment couch can not only be translated up and down, left and right, and front and back, but also can be rotated up and down, left and right, and front and back), so when the computer adjusts the position of the treatment couch according to the deviation, the treatment couch can be translated according to the translation data in the deviation; if the treatment couch is a six-dimensional treatment couch, the treatment couch can be rotated according to the angle data in the deviation; and if the treatment couch is a three-dimensional treatment couch, the angle data in the deviation can be converted into translation data, and the treatment couch is translated according to the translation data converted. The conversion of the angle data into the translation data can be implemented according to the sine and cosine theorem of a triangle, which will not be repeated in the embodiment of the present disclosure.

For example, it is assumed that the treatment couch is a three-dimensional treatment couch, the translation data in the deviation is: X=2 mm, Y=0, Z=−1 mm, and the angle data is: XY=0, YZ=1°, XZ=2°. Then, the computer can control the treatment couch to translate 2 mm in the positive direction of the X axis and translate 1 mm in the negative direction of the Z axis. In addition, the computer can also convert the angle data into translation data, and then translate the treatment couch according to the angle data converted.

In the embodiment of the present disclosure, the computer may not be able to ensure that the position of the treatment body part meets the requirement of treatment precision by single adjustment. Therefore, in order to ensure the precision of alignment, the IGRT system and the computer can adjust the position of the treatment couch multiple times.

Optionally, after adjusting the position of the treatment couch according to the deviation, the computer may send an image guide instruction to the IGRT system again, and the IGRT system may perform the method shown in steps 305 to 307 again according to the received image guide instruction, so that the computer can update the deviation received last time according to the deviation received each time, and readjust the position of the treatment couch according to the latest deviation received.

When the computer detects that the received deviation is smaller than the preset deviation threshold, it can be determined that the position of the treatment body part has met the requirements, and the position of the treatment couch does not need to be adjusted again, so the next treatment process can be continued, for example, step 309 can be performed.

It should be noted that, after adjusting the position of the treatment couch so that the position of the treatment body part meets the requirements (for example, the filming point of the DRR image coincides with the imaging point of the IGRT system), the computer may also obtain current coordinates of the treatment couch, and store the corresponding relationship between the target region and the coordinates of the treatment couch at the current gamma angle. If the computer detects the same gamma angle as the current gamma angle again in the same treatment plan, then when the computer executes the above step 303, it can directly adjust the position of the treatment couch according to the coordinates corresponding to the target region at the current gamma angle, and transfer the treatment body part of the patient to the imaging area of the IGRT system. Since the coordinates have been verified by the IGRT system during the last treatment process, it can effectively improve the efficiency of subsequent readjustment, that is, effectively reduce the number of repetitions required for steps 304 to 308 described above.

For example, assuming that the current gamma angle is 70°, and when the filming point of the DRR image coincides with the imaging point of the IGRT system, the coordinates of the treatment couch are (x1, y1, z1), then the computer can record the corresponding coordinates of the treatment couch as (x1, y1, z1) when the gamma angle is 70°. When the computer detects the gamma angle of 70° again in the same treatment plan, it can directly adjust the position of the treatment couch according to the coordinates (x1, y1, z1).

It should also be noted that, in the embodiment of the present disclosure, the computer may also detect the translation data and angle data in the received deviation before adjusting the position of the treatment couch. When the computer detects that any sub-data in the angle data is greater than a preset angle threshold (for example, 3°), or detects that any sub-data in the translation data is greater than a preset translation threshold, the computer may display warning information. The warning information may prompt the therapist that the current offset of the treatment couch is large, and the patient needs to be repositioned.

Step 309, the computer controls the treatment couch and a collision detection device to perform collision simulation detection when the deviation is smaller than the preset deviation threshold.

In the embodiment of the present disclosure, after the IGRT system and the computer complete the positioning of the patient, in order to avoid the collision between the patient and the treatment gantry during the treatment process, the computer may also control the treatment couch and the collision detection device to perform collision simulation detection. Optionally, the therapist may first plug in the collision detection device (such as an anti-collision detection rocker), and then the computer may move the treatment couch, so that the target region is aligned with a virtual beam focus in the collision detection device. The therapist (or the computer) may then control the collision detection device to move according to a preset trajectory (for example, to rotate around the treatment couch), to detect whether the collision detection device collides with the patient (or the attachment of the head fixing device).

Step 310, a radiation therapy operation is started when the result of the collision simulation detection that the detection succeeds is detected.

Step 311, the radiation therapy operation is suspended when the result of the collision simulation detection that the detection fails is detected.

After the collision detection device completes the collision simulation detection, the therapist can determine according to the number of collisions whether the result of the collision simulation detection can be received, and the therapist can indicate the result of the collision simulation detection to the computer through a preset operation, where the result may be that the detection succeeds or fails. If the computer detects the result that the detection succeeds, the radiation therapy can be continued, that is, step 312 can be continued. If the result of the collision simulation detection that the detection fails is detected, the treatment process may be suspended to reposition the patient or recheck the treatment plan.

For example, after the collision simulation detection is completed, the touch display screen of the computer may display an icon indicating that the detection succeeds, and an icon indicating that the detection fails, and the therapist may click any of the icons to indicate the result of the collision simulation detection by the computer.

As mentioned above, in each treatment plan, the patient may be treated under multiple gamma angles. Therefore, when the treatment plan includes multiple gamma angles, the IGRT system and the computer may execute the method shown in the above steps 301 to 311 to complete the position verification and collision detection for each gamma angle.

For example, assuming that the gamma angles in the treatment plan are respectively 70°, 90° and 110°, and the current gamma angle is 70°, after the computer completes the anti-collision detection at the 70° gamma angle, the therapist may adjust the current gamma angle to 90°, the operator exits the treatment room and closes a protective door of the treatment room, and then the position verification and collision detection at the 90° gamma angle can be performed through the method shown in steps 301 to 311 above.

After the computer completes the anti-collision detection at the 90° gamma angle, the therapist can adjust the current gamma angle to 110°, the operator exits the treatment room and closes the protective door of the treatment room, and then the position verification and collision detection at the 110° gamma angle can be performed through the method shown in steps 301 to 311 above.

Step 312, the computer calculates a second offset between a target region and a beam focus.

After completing the positioning and collision detection, when the radiation therapy begins, because the imaging point of the current IGRT system has been aligned with the filming point of the reconstructed image, and also because the relative position relationship between the imaging point of the IGRT system and the beam focus is constant, and the computer can also determine the relative position relationship between the filming point of the image and the target region according to the file transmitted by the TPS, the computer can calculate the second offset between the target region and the beam focus according to the two relative position relationships.

Similarly, the second offset may include translation data and angle data, the translation data may include three sub-data, and each sub-data may be used to indicate an offset of the treatment couch in the preset three-dimensional coordinate system along each coordinate axis; the angle data may also include three sub-data, and each sub-data is used to indicate an amount of rotation of the treatment couch in the three-dimensional coordinate system within each plane.

It should be noted that, in the embodiment of the present disclosure, the second offset may also be calculated by the IGRT system. For example, after aligning the filming point of the reconstructed image with the imaging point of the IGRT system by adjusting the position of the treatment couch, the computer may send a calculation instruction to the IGRT system before the radiation therapy; and the IGRT system may calculate, after receiving the calculation instruction, the second offset between the target region and the beam focus according to the relative position relationship between the imaging point of the IGRT system and the beam focus, and the relative position relationship between the filming point of the image and the target region, and send the second offset to the computer.

Step 313, the computer adjusts the position of the treatment couch according to the second offset, so that the target region is aligned with the beam focus.

In the embodiment of the present disclosure, since the second offset may include translation data and angle data, when the computer adjusts the position of the treatment couch according to the second offset, it may translate the treatment couch according to the translation data in the second offset; if the treatment couch is a six-dimensional treatment couch, the computer may rotate the treatment couch according to the angle data in the second offset; and if the treatment couch is a three-dimensional treatment couch, the computer may convert the angle data in the deviation into translation data, and then translate the treatment couch according to the translation data converted, so that the target region is finally aligned with the beam focus. After that, radiation therapy may be started.

In an optional implementation manner, after the IGRT system and the computer complete the position verification and collision detection for all gamma angles by performing the above steps 301 to 311 cyclically, if they do not exit the treatment plan, they can directly perform the treatment operation at the current gamma angle, that is, directly perform steps 312 and 313. Or, the therapist may choose to perform position verification again, that is, control the IGRT system and the computer to perform the methods shown in steps 304 to 308 again to correct the position of the treatment couch again, and then perform the treatment operation after completing the position verification.

In another optional implementation manner, after the IGRT system and the computer complete the position verification and collision detection for all gamma angles, if they exit the treatment plan, the computer may acquire, according to a detected gamma angle, pre-stored coordinates corresponding to the detected gamma angle when receiving the treatment plan again, adjust the position of the treatment couch according to the coordinates, and then perform the methods shown in steps 304 to 308 in order to complete the position verification of the patient. After that, the radiation therapy system can start the treatment operation.

It should be noted that when the treatment couch in the radiation therapy system is a three-dimensional treatment couch, the computer may first adjust, after receiving the deviation sent by the IGRT system each time, the position of the treatment couch according to the translation data in the deviation, but does not process the angle data in the deviation. The computer may retrieve the latest stored deviation (that is, the deviation sent by the IGRT system last time) before the treatment starts, convert the angle data in the deviation into translation data, and then adjust the position of the treatment couch according to the translation data converted. After that, the computer may adjust the position of the treatment couch again through the methods shown in steps 312 and 313 above, so that the target region is aligned with the beam focus, and then the treatment operation may be started.

Further, after completing the treatment of each target region at a certain gamma angle, the radiation therapy system may perform the following cyclic operations: the therapist may open the protective door and adjust the current gamma angle; the computer obtains, after detecting the adjusted gamma angle, pre-stored coordinates corresponding to the adjusted gamma angle, adjust the position of the treatment couch according to the coordinates, and then perform the methods shown in steps 304 to 308 in order to complete the position verification of the patient. After that, the computer may perform the methods shown in steps 312 and 313 again to align the target region with the beam focus. Finally, the radiation therapy system may start the treatment operation at the gamma angle.

For other gamma angles in the treatment plan, the radiation therapy system may repeat the cyclic operations in order until the treatment of target regions for all gamma angles is completed.

When the patient is treated again later, the radiation therapy system may perform the cyclic operations until the treatment of the target regions under all gamma angles of treatment (single or fractional treatment) is completed.

It should be noted that the order of the steps of the positioning method provided by the embodiment of the present disclosure may be adjusted appropriately, and the steps may also be increased or decreased according to the situation. For example, step 303 may be performed simultaneously with step 302; steps 309 to 311 may be deleted according to the situation, and step 312 may also be performed by the IGRT system. The modified methods readily conceived by any skilled person who is familiar with this art within the disclosed technical scope of the present invention shall fall into the protection scope of the present disclosure, so details are not repeated again.

Based on the above, the embodiment of the present disclosure provides a positioning method, in which a computer may receive a deviation sent by an image guide system, the deviation being obtained by comparing, after the image guide system acquires a reconstructed image corresponding to the current gamma angle, an IGRT image corresponding to the current gamma angle with the reconstructed image; and the computer may adjust the position of the treatment body part according to the deviation when the deviation is greater than a preset threshold. Since the image referenced by the image guide system when calculating the deviation is a reconstructed image reconstructed according to an image and corresponding to the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced as much as possible.

Figure 9:
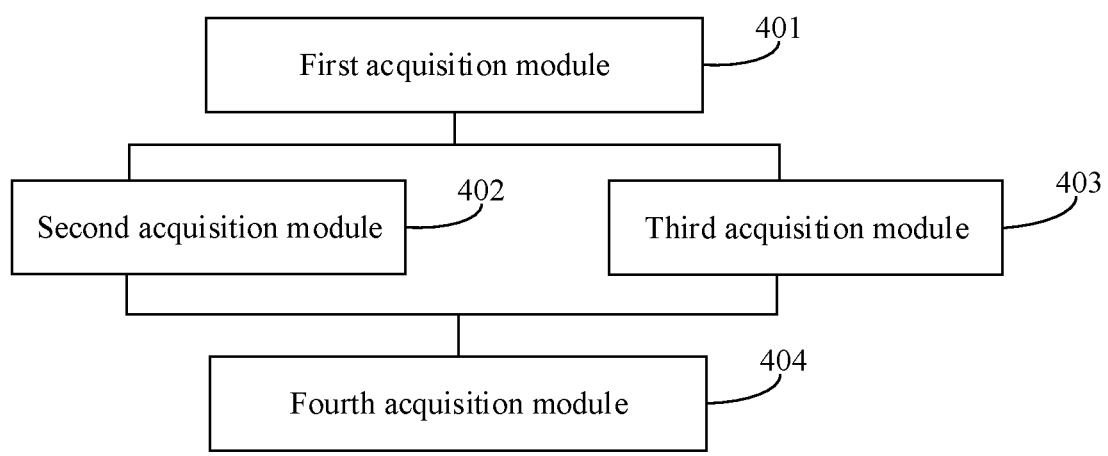
FIG. 9 is a schematic structural diagram of an image guide system according to an embodiment of the present disclosure.

FIG. 9 is a schematic structural diagram of an image guide system provided by an embodiment of the present invention. The image guide system may be applied to the radiation therapy system shown in FIG. 1. Referring to FIG. 9, the image guide system may include:

a first acquisition module 401, configured to acquire a current gamma angle;

a second acquisition module 402, configured to acquire a reconstructed image corresponding to the current gamma angle, the reconstructed image being an image reconstructed according to an image of a treatment body part acquired in advance;

a third acquisition module 403, configured to acquire an IGRT image of the treatment body part corresponding to the current gamma angle, the IGRT image being an image generated by the image guide system, where the third acquisition module 403 may include multiple sets of image acquisition units; and a fourth acquisition module 404, configured to compare the reconstructed image with the IGRT image to obtain a deviation of a position of the treatment body part, and to send out the deviation, so that the position of the treatment body part is adjusted according to the deviation when the deviation is greater than a preset threshold.

Optionally, the first acquisition module 401 may be configured to:

acquire a treatment plan that includes at least one gamma angle; and determine the current gamma angle from the at least one gamma angle.

Figure 10:
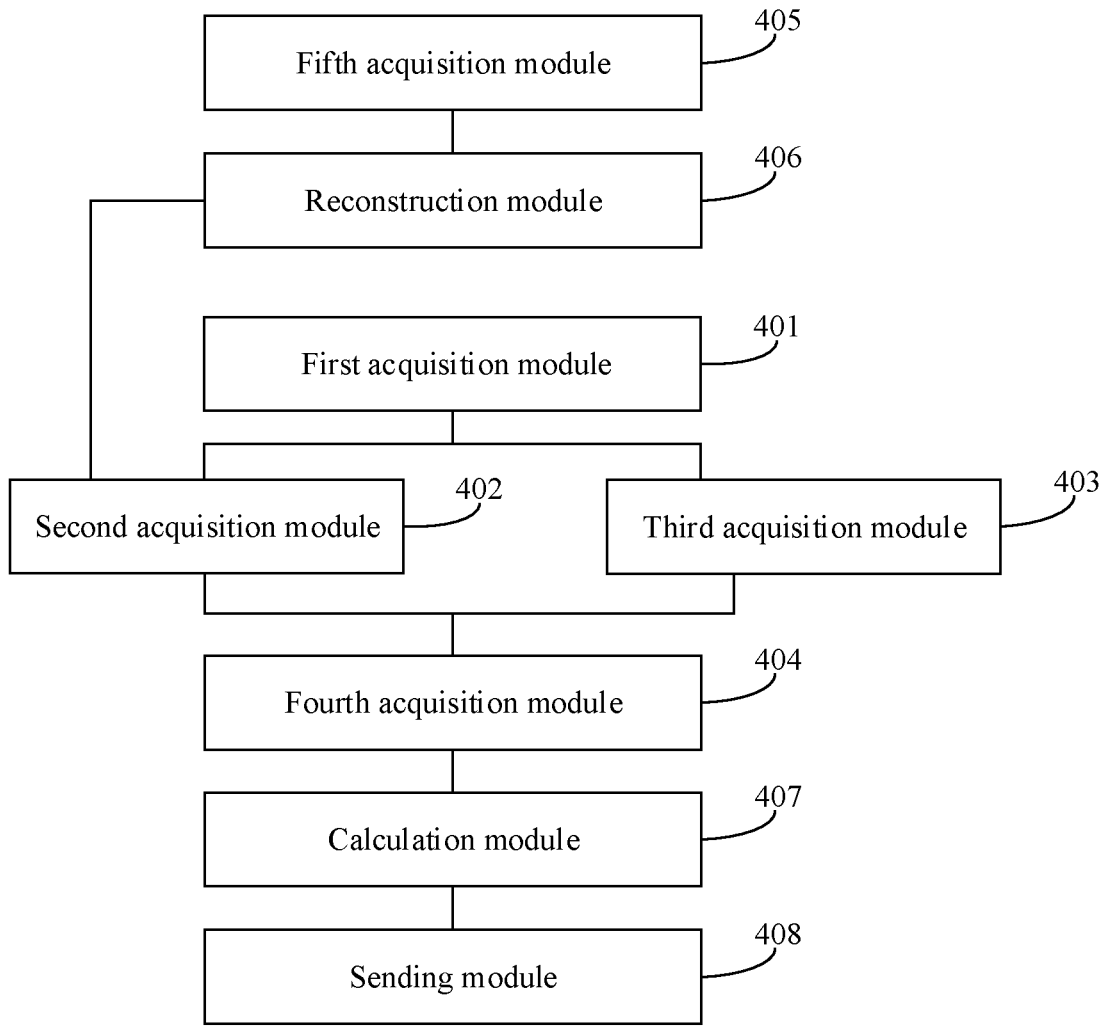
FIG. 10 is a schematic structural diagram of another image guide system according to an embodiment of the present disclosure.

Optionally, as shown in FIG. 10, the image guide system may further include:

a fifth acquisition module 405, configured to acquire the image of the treatment body part before the reconstructed image corresponding to the current gamma angle is acquired; and a reconstruction module 406, configured to reconstruct a reconstructed image corresponding to each of the at least one gamma angle according to the image of the treatment body part.

Correspondingly, the second acquisition module 402 may be configured to:

acquire the reconstructed image corresponding to the current gamma angle from the reconstructed images corresponding to the at least one gamma angle.

Optionally, the reconstruction module 406 may be configured to:

determine a rotation axis according to a filming point preset in the image, the rotation axis being a designated coordinate axis of a coordinate system where the filming point is located, or a linear axis parallel to the designated coordinate axis; and rotate the image about the rotation axis by a deflection angle to obtain the reconstructed image corresponding to the gamma angle, the deflection angle being a deflection angle between the gamma angle and a gamma angle when the image is acquired.

Preferably, the fourth acquisition module 404 may be configured to:

compare the reconstructed image with the IGRT image, and calculate a first offset between the filming point in the reconstructed image and an imaging point of the image guide system; and send the first offset to the computer as the deviation of the position of the treatment body part.

Optionally, as shown in FIG. 10, the image guide system may further include:

a calculation module 407, configured to calculate a second offset between a beam focus of the radiation source and a target region according to a relative position relationship between the imaging point of the image guide system and the beam focus of the radiation source, and a relative position relationship between the filming point in the image and the target region.

a sending module 408, configured to send the second offset to the computer, so that the computer adjusts the position of a treatment couch according to the second offset, to align the beam focus with the target region.

Based on the above, the embodiment of the present disclosure provides an image guide system, the image guide system may acquire, after acquiring a current gamma angle, a reconstructed image corresponding to the current gamma angle, the reconstructed image corresponding to the current gamma angle being an image reconstructed by the image guide system in advance according to an image of a treatment body part; and then the image guide system may determine a deviation of the position of the treatment body part by comparing an IGRT image corresponding to the current gamma angle with the reconstructed image, and send out the deviation, so that an adjustment device can adjust the position of the treatment body part according to the deviation when the deviation is greater than a preset threshold, to position the patient. Since the image referenced by the image guide system when calculating the deviation is a reconstructed image reconstructed according to an image and corresponding to the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced.

Figure 11:
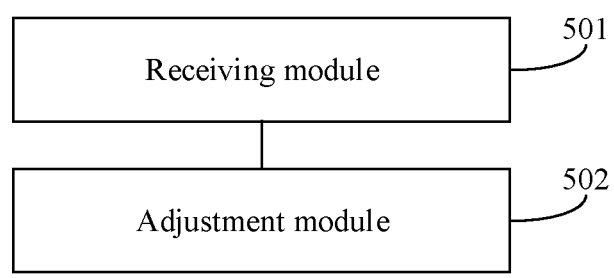
FIG. 11 is a schematic structural diagram of a computer according to an embodiment of the present disclosure.

FIG. 11 is a schematic structural diagram of a computer provided by an embodiment of the present disclosure. The computer may be applied to the radiation therapy system shown in FIG. 1. Referring to FIG. 11, the computer may include:

a receiving module 501, configured to receive a deviation of a position of a treatment body part sent by an image guide system, the deviation being obtained by comparing a reconstructed image corresponding to a current gamma angle with an IGRT image of the treatment body part at the current gamma angle after the reconstructed image and the IGRT image are acquired by the image guide system, and the reconstructed image being an image reconstructed according to an image of the treatment body part acquired in advance; and an adjustment module 502, configured to adjust the position of the treatment body part according to the deviation when the deviation is greater than a preset threshold.

Figure 12:
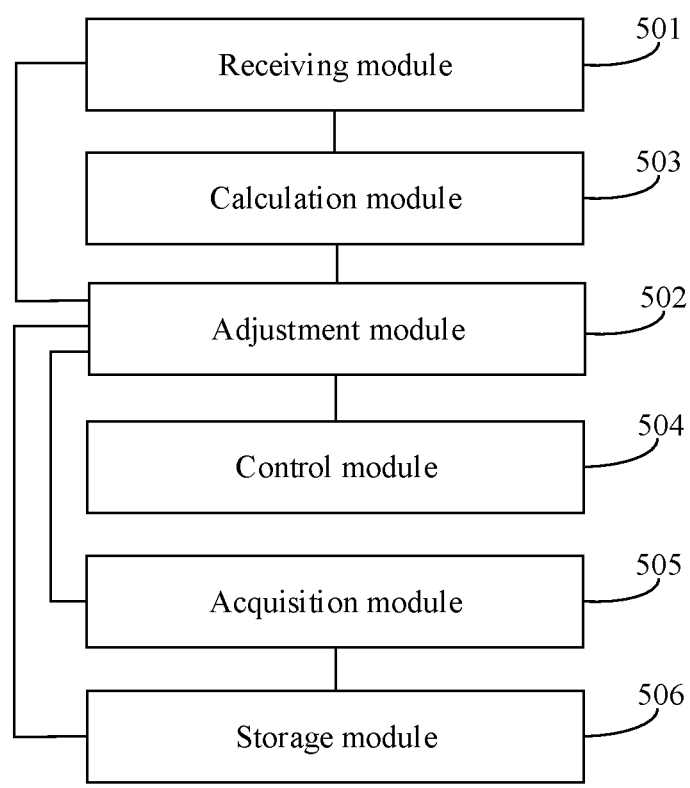
FIG. 12 is a schematic structural diagram of another computer according to an embodiment of the present disclosure.

Optionally, the deviation may be a first offset between a filming point in the reconstructed image and an imaging point of the image guide system. As shown in FIG. 12, the computer may further include:

a calculation module 503, configured to calculate, after the deviation of the position of the treatment body part sent by the image guide system is received, a second offset between a beam focus of the radiation source and a target region according to a relative position relationship between the imaging point of the image guide system and the beam focus of the radiation source, and a relative position relationship between the filming point in the image and the target region.

Correspondingly, the adjustment module 502 may also be configured to adjust a position of a treatment couch according to the second offset, so that the beam focus is aligned with the target region.

Optionally, as shown in FIG. 12, the computer may further include:

a control module 504, configured to control the treatment couch and a collision detection device to perform collision simulation detection after the position of the treatment body part is adjusted according to the deviation; start a radiation therapy operation when the result of the collision simulation detection that the detection succeeds is detected; and suspend the radiation therapy when the result of the collision simulation detection that the detection fails is detected.

Optionally, the deviation includes translation data and angle data, and the adjustment module 502 may be configured to:

translate the treatment couch according to the translation data; and rotate the treatment couch according to the angle data, or convert the angle data into translation data, and translate the treatment couch according to the converted translation data.

Optionally, as shown in FIG. 12, the computer may further include:

an acquisition module 505, configured to acquire coordinates of the treatment couch after the position of the treatment body part is adjusted; and a storage module 506, configured to store a corresponding relationship between the target region and the coordinates of the treatment couch at the current gamma angle.

Correspondingly, the adjustment module 502 may be further configured to: adjust the position of the treatment couch according to the coordinates corresponding to the current gamma angle when the same gamma angle as the current gamma angle is detected again in the same treatment plan.

Based on the above, the embodiment of the present disclosure provide a computer, the computer may receive a deviation sent by an image guide system, the deviation being obtained by comparing, after the image guide system acquires a reconstructed image corresponding to the current gamma angle, an IGRT image corresponding to the current gamma angle with the reconstructed image; and the computer may adjust the position of the treatment body part according to the deviation when the deviation is greater than a preset threshold. Since the image referenced by the image guide system when calculating the deviation is a reconstructed image reconstructed according to an image at the current gamma angle, the precision of positioning based on the deviation determined from the reconstructed image is high, and the effect of radiation therapy can be guaranteed. In addition, because images of the treatment body part at different gamma angles do not need to be acquired, the increase in radiation dose received by the patient can be avoided, and the influence of radiation on the patient's health can be reduced as much as possible.

Those skilled in the art could clearly understand that, for convenience and briefness of description, the specific working processes of the above-described image guide system and computer may be referenced to the corresponding processes in the embodiments of the aforementioned methods, and details are not described herein again.

An embodiment of the present disclosure further provides an image guide system. The image guide system may include: a processor and a memory, where the memory is configured to store instructions executed by the processor, and the processor may be used to implement the positioning method shown in FIG. 4, or the steps performed by the IGRT system in the positioning method shown in FIG. 6.

An embodiment of the present disclosure further provides a computer. The computer may be, for example, a host computer in a radiation therapy system. The computer may include a processor and a memory, where the memory is configured to store instructions executed by the processor, and the processor may be used to implement the positioning method shown in FIG. 5, or the steps performed by the computer in the positioning method shown in FIG. 6.

An embodiment of the present disclosure further provides a radiation therapy system. Referring to FIG. 1, the system may include: a computer 02 and an image guide system 01, and the computer 02 establishes a communication connection with the image guide system 01.

The image guide system 01 may be the system shown in FIG. 9 or 10, and the computer may be the computer shown in FIG. 11 or 12.

Those skilled in the art could understand that all or some of the steps in the above embodiments may be completed either by hardware, or by a program instructing related hardware. The program may be stored in a computer-readable storage medium. The above-mentioned storage medium may be a read-only memory, a magnetic disk or an optical disk, etc. When the computer-readable storage medium runs on the computer, the computer performs the positioning method as shown in any one of FIGS. 4 to 6.

The above descriptions are merely the preferred embodiments of the present disclosure, and are not intended to limit the present disclosure. Any modification, equivalent substitution, improvement or the like made within the spirit and principle of the present disclosure shall fall within the protection scope of the present disclosure.

What is claimed is:

1. A positioning method, comprising:
    acquiring a current gamma angle before radiation beams of a radiation source irradiate a treatment body part of a patient, the gamma angle being an angle between a vertical plane and a supporting plane of a fixing structure for supporting the treatment body part of the patient, and the current gamma angle being less than 90° or greater than 90°;
    acquiring a reconstructed image corresponding to the current gamma angle, the reconstructed image being an image reconstructed according to an image of the treatment body part acquired in advance with the gamma angle being 90°;
    acquiring an image guide radiation therapy (IGRT) image of the treatment body part with the treatment body part being supported by the supporting plane at the current gamma angle, wherein the IGRT image is an image generated by an image guide system; and
    comparing the reconstructed image with the IGRT image to obtain a deviation of a position of the treatment body part so that the position of the treatment body is adjusted according to the deviation when the deviation is greater than a preset threshold.

2. The method according to claim 1, wherein the acquiring a current gamma angle before radiation beams of a radiation source irradiate a treatment body part of a patient comprises:
acquiring a treatment plan that includes at least one gamma angle; and
determining the current gamma angle from the at least one gamma angle in the treatment plan.

3. The method according to claim 2, wherein:
before acquiring the reconstructed image corresponding to the current gamma angle, the method further comprises:
acquiring the image of the treatment body part with the gamma angle being 90°; and
acquiring a reconstructed image corresponding to each of the at least one gamma angle in the treatment plan according to the image of the treatment body part with the gamma angle being 90°; and
the acquiring a reconstructed image corresponding to the current gamma angle comprises:
acquiring the reconstructed image corresponding to the current gamma angle from the reconstructed images corresponding to the at least one gamma angle in the treatment plan.

4. The method according to claim 3, wherein the acquiring a reconstructed image corresponding to each of the at least one gamma angle in the treatment plan according to the image of the treatment body part comprises:
determining a rotation axis according to a predetermined point in the image of the treatment body part, the rotation axis being a designated coordinate axis of a coordinate system where the predetermined point is located, or a linear axis parallel to the designated coordinate axis; and
rotating the image of the treatment body part about the rotation axis by a deflection angle to obtain the reconstructed image corresponding to each of the at least one gamma angle in the treatment plan, the deflection angle being a deflection angle between each of the at least one gamma angle in the treatment plan and the gamma angle at which the image of the treatment body part is acquired in advance.

5. The method according to claim 1, wherein the comparing the reconstructed image with the IGRT image to obtain a deviation of the position of the treatment body part comprises:
comparing the reconstructed image with the IGRT image, and calculating a first offset between a predetermined point in the reconstructed image and an imaging point of the image guide system; and
sending the first offset to a computer as the deviation of the position of the treatment body part.

6. The method according to claim 5, further comprising:
calculating a second offset between a beam focus of the radiation source for treating treatment body part of the patient and a target region of the treatment body part according to a relative position relationship between the imaging point of the image guide system and the beam focus of the radiation source, and a relative position relationship between the predetermined point in the image and the target region; and
sending the second offset to the computer, so that the computer adjusts the position of a treatment couch according to the second offset, to align the beam focus with the target region.

7. The positioning method according to claim 6, wherein the image guide system comprises a plurality of sets of image acquisition units, each of the plurality of sets of image acquisition units comprises a detector and a bulb, rays emitted by the bulbs of the plurality of sets of image acquisition units intersect at the imaging point, and the imaging point of the image guide system and the beam focus of the radiation source are both fixed.

8. od according to claim 1, further comprising: adjusting the fixing structure such that the treatment body part being supported by the supporting plane at the acquired current gamma angle.

9. A positioning method, comprising:
receiving a deviation of a position of a treatment body part of a patient sent by an image guide system, the deviation being obtained by comparing a reconstructed image corresponding to a current gamma angle with an image guide radiation therapy (IGRT) image of the treatment body part corresponding to the current gamma angle after the reconstructed image and the IGRT image are acquired by the image guide system, wherein the gamma angle is an angle between a vertical plane and a supporting plane of a fixing structure for supporting the treatment body part, the IGRT image of the treatment body part is acquired with the treatment body part of the patient being supported by the supporting plane at the current gamma angle, the current gamma angle is less than 90° or greater than 90°, and the reconstructed image is an image reconstructed according to an image of the treatment body part acquired in advance with the gamma angle being 90°; and
adjusting the position of the treatment body part according to the deviation when the deviation is greater than a preset threshold.

10. The method according to claim 9, wherein the deviation is a first offset between a predetermined point in the reconstructed image and an imaging point of the image guide system;
after receiving the deviation of the position of the treatment body part sent by the image guide system, the method further comprises:
calculating a second offset between a beam focus of radiation source and a target region according to a relative position relationship between the imaging point of the image guide system and the beam focus of the radiation source, and a relative position relationship between the predetermined point in the image and the target region; and
adjusting a position of a treatment couch according to the second offset, so that the beam focus is aligned with the target region.

11. The method according to claim 10, wherein after adjusting the position of the treatment couch according to the second offset, the method further comprises:
controlling the treatment couch and a collision detection device to perform collision simulation detection;
starting a radiation therapy operation when a result of the collision simulation detection that the detection succeeds is detected; or
suspending the radiation therapy operation when the result of the collision simulation detection that the detection fails is detected.

12. The method according to claim 9, wherein the deviation comprises translation data and angle data, and the adjusting the position of the treatment body part according to the deviation comprises:
translating the treatment couch according to the translation data; and rotating the treatment couch according to the angle data, or converting the angle data into translation data, and translating the treatment couch according to the converted translation data.

13. An image guide system, comprising a processor and a memory, wherein the memory is configured to store instructions executed by the processor, and the processor is configured to perform operations of:
acquiring a current gamma angle before radiation beams of radiation source irradiate a treatment body part of a patient, wherein the gamma angle is an angle between a vertical plane and a supporting plane of a fixing structure for supporting the treatment body part, and the current gamma angle is less than 90° or greater than 90°;
acquiring a reconstructed image corresponding to the current gamma angle, the reconstructed image being an image reconstructed according to an image of the treatment body part acquired in advance with the gamma angle being 90°;
acquiring an IGRT image of the treatment body part with the treatment body part being supported by the supporting plane at the current gamma angle, the IGRT image being an image generated by the image guide system; and
comparing the reconstructed image with the IGRT image to obtain a deviation of a position of the treatment body part so that the position of the treatment body part is adjusted according to the deviation when the deviation is greater than a preset threshold.

14. The system according to claim 13, wherein the processor is further configured to perform operations of:
acquiring a treatment plan that comprises at least one gamma angle; and
determining the current gamma angle from the at least one gamma angle in the treatment plan.

15. The system according to claim 14, wherein
the processor is further configured to perform operations of:
acquiring the image of the treatment body part with the gamma angle being 90° before the reconstructed image corresponding to the current gamma angle is acquired; and
acquiring a reconstructed image corresponding to each of the at least one gamma angle according to the image of the treatment body part;
the operation of acquiring a reconstructed image corresponding to the current gamma angle comprises:
acquiring the reconstructed image corresponding to the current gamma angle from the reconstructed images corresponding to the at least one gamma angle.

16. The system according to claim 15, wherein the operation of acquiring a reconstructed image corresponding to each of the at least one gamma angle in the treatment plan according to the image of the treatment body part comprises:
determining a rotation axis according to a predetermined point in the image of the treatment body part, the rotation axis being a designated coordinate axis of a coordinate system where the predetermined point is located, or a linear axis parallel to the designated coordinate axis; and
rotating the image of the treatment body part about the rotation axis by a deflection angle to obtain the reconstructed image corresponding to each of the at least one gamma angle in the treatment plan, the deflection angle being a deflection angle between each of the at least one gamma angle in the treatment plan and the gamma angle at which the image of the treatment body part is acquired in advance.

17. The system according to claim 13, wherein the operation of comparing the reconstructed image with the IGRT image to obtain a deviation of the position of the treatment body part comprises:
comparing the reconstructed image with the IGRT image, and calculating a first offset between a predetermined point in the reconstructed image and an imaging point of the image guide system; and
sending the first offset to a computer as the deviation of the position of the treatment body part,
wherein the processor is further configured to perform operations of:
calculating a second offset between a beam focus of the radiation source for treating treatment body part of the patient and a target region of the treatment body part according to a relative position relationship between the imaging point of the image guide system and the beam focus of the radiation source, and a relative position relationship between the predetermined point in the image and the target region; and
sending the second offset to the computer, so that the computer adjusts the position of a treatment couch according to the second offset, to align the beam focus with the target region.

18. A computer, the computer comprising a processor and a memory, wherein the memory is configured to store instructions executed by the processor, and the processor is configured to perform operations of:
receiving a deviation of a position of a treatment body part of a patient sent by an image guide system of a radiation therapy system, the deviation being obtained by comparing a reconstructed image corresponding to a current gamma angle with an IGRT image corresponding to the current gamma angle after the reconstructed image and the IGRT image are acquired by the image guide system, wherein the gamma angle is an angle between a vertical plane and a supporting plane of a fixing structure for supporting the treatment body part, the IGRT image of the treatment body part is acquired with the treatment body part of the patient being supported by the supporting plane at the current gamma angle, the current gamma angle is less than 90° or greater than 90° and the reconstructed image is an image reconstructed according to an image of the treatment body part acquired in advance with the gamma angle being 90°; and
adjusting the position of the treatment body part according to the deviation when the deviation is greater than a preset threshold.

19. The computer according to claim 18, wherein the deviation is a first offset between a predetermined point in the reconstructed image and an imaging point of the image guide system;
the processor is further configured to perform operations of:
calculating, after receiving the deviation of the position of the treatment body part sent by the image guide system, a second offset between a beam focus of radiation source and a target region according to a relative position relationship between the imaging point of the image guide system and the beam focus of the radiation source, and a relative position relationship between the predetermined point in the image and the target region; and adjusting a position of a treatment couch according to the second offset, so that the beam focus is aligned with the target region.

20. The computer according to claim 18, wherein the deviation comprises translation data and angle data, and the operation of adjusting the position of the treatment body part according to the deviation comprises:
   translating the treatment couch according to the translation data; and
   rotating the treatment couch according to the angle data, or converting the angle data into translation data, and translating the treatment couch according to the converted translation data.

\* \* \* \* \*